(12) United States Patent
Kim

(10) Patent No.: US 10,517,916 B2
(45) Date of Patent: Dec. 31, 2019

(54) COMPOSITION FOR PREVENTING, ALLEVIATING OR TREATING NEURODEGENERATIVE DISEASES

(71) Applicant: WONKWANG UNIVERSITY CENTER FOR INDUSTRY-ACADEMY COOPERATION, Iksan-si, Jeollabuk-do (KR)

(72) Inventor: Sung Chul Kim, Seoul (KR)

(73) Assignee: Wonkwang University Center for Industry-Academy Cooperation, Iksan-si, Jeollabuk-do (KR)

( * ) Notice: Subject to any disclaimer, the term of this patent is extended or adjusted under 35 U.S.C. 154(b) by 0 days.

(21) Appl. No.: 15/548,791

(22) PCT Filed: Aug. 25, 2015

(86) PCT No.: PCT/KR2015/008847
§ 371 (c)(1),
(2) Date: Aug. 4, 2017

(87) PCT Pub. No.: WO2016/195164
PCT Pub. Date: Dec. 8, 2016

(65) Prior Publication Data
US 2018/0092958 A1    Apr. 5, 2018

(30) Foreign Application Priority Data

Jun. 3, 2015  (KR) ........................ 10-2015-0078512

(51) Int. Cl.
| | | |
|---|---|---|
| *A61K 36/9066* | (2006.01) | |
| *A61K 36/8988* | (2006.01) | |
| *A61K 36/284* | (2006.01) | |
| *A61K 36/484* | (2006.01) | |
| *A61K 36/537* | (2006.01) | |
| *A61K 36/65* | (2006.01) | |
| *A61K 36/69* | (2006.01) | |
| *A61K 36/732* | (2006.01) | |
| *A61P 25/28* | (2006.01) | |

(52) U.S. Cl.
CPC ........ *A61K 36/9066* (2013.01); *A61K 36/284* (2013.01); *A61K 36/484* (2013.01); *A61K 36/537* (2013.01); *A61K 36/65* (2013.01); *A61K 36/69* (2013.01); *A61K 36/732* (2013.01); *A61K 36/8988* (2013.01); *A61P 25/28* (2018.01); *A61K 2236/33* (2013.01); *A61K 2236/51* (2013.01)

(58) Field of Classification Search
None
See application file for complete search history.

(56) References Cited

FOREIGN PATENT DOCUMENTS

| | | |
|---|---|---|
| KR | 10-1999-0018942 A | 3/1999 |
| KR | 10-2002-0066173 A | 8/2002 |
| KR | 10-2004-0023196 A | 3/2004 |
| KR | 10-2005-0047779 A | 5/2005 |
| KR | 10-2005-0101818 A | 10/2005 |
| KR | 10-2006-0023885 A | 3/2006 |
| KR | 10-0564904 B1 | 7/2006 |
| KR | 10-2007-0040209 A | 4/2007 |

OTHER PUBLICATIONS

Google Patents translation of KR1020050047779. (Year: 2005).*
Google Patents translation of KR1020070040209. (Year: 2007).*
Iwasaki, et al., JAGS, 52:1518. (Year: 2004).*
Shin Hee Han et al., "Therapeutic Effect of the Mixed Extract of Panax ginseng C.A. Mey. and Chaenomeles sinensis Koehne on the Injury of Brain Tissue in the Mice by Alzheimer's Disease", Korean Journal of Plant Resources, vol. 20, No. 4, pp. 325-330, 2007, English abstract.
Dong-sung Lee et al., "KCHO-1, a Novel Antineuroinflammatory Agent, Inhibits Lipopolysaccharide-Induced Neuroinflammatory Responses through Nrf2-Mediated Heme Oxygenase-1 Expression in Mouse BV2 Microglia Cells", Evidence-Based Complementary and Alternative Medicine, vol. 2014, Article ID 357154, pp. 1-11, 2014.
Sung-Chul Kim et al., "The follow-up study on patients of Amyotrophic lateral sclerosis after 1 year", Journal of Korean Pharmacopuncture Institute, vol. 13, No. 1, Mar. 2010, English abstract.
Hohyun Jeong et al., "A Study on the Oral Toxicity of Mecasin in Rats", Journal of Pharmacopuncture, pp. 061-065, 2014.

(Continued)

*Primary Examiner* — Michael Barker
(74) *Attorney, Agent, or Firm* — Rabin & Berdo, P.C.

(57) ABSTRACT

Disclosed herein is a pharmaceutical composition for preventing, alleviating or treating neurodegenerative diseases. The pharmaceutical composition contains, as active ingredients, Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum. The pharmaceutical composition is prepared by a method including the steps of: mixing Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum to obtain a mixture, and extracting the mixture to obtain a mixture extract; filtering the mixture extract; concentrating the mixture extract; and drying the mixture extract.

11 Claims, 4 Drawing Sheets

(56) References Cited

OTHER PUBLICATIONS

Myung Geun Kook et al., "KCHO-1(Mecasin), a novel herbal anti-inflammatory compound, attenuates oxidative 5 stress in an animal model of amyotrophic lateral sclerosis", Journal of Veterinary Science, Apr. 6, 2017.

Sung-chul Kim et al., "A pilot clinical study on the Traditional Korean Medicine treatment of Amyotrophic lateral sclerosis", Journal of Korean Pharmacopuncture Institute, vol. 12, No. 1, Mar. 2009, English abstract.

Dong-Sung Lee et al., "The herbal extract KCHO-1 exerts a neuroprotective effect by ameliorating oxidative stress via heme oxygenase-1 upregulation", Molecular Medicine Reports, Jun. 2016.

\* cited by examiner

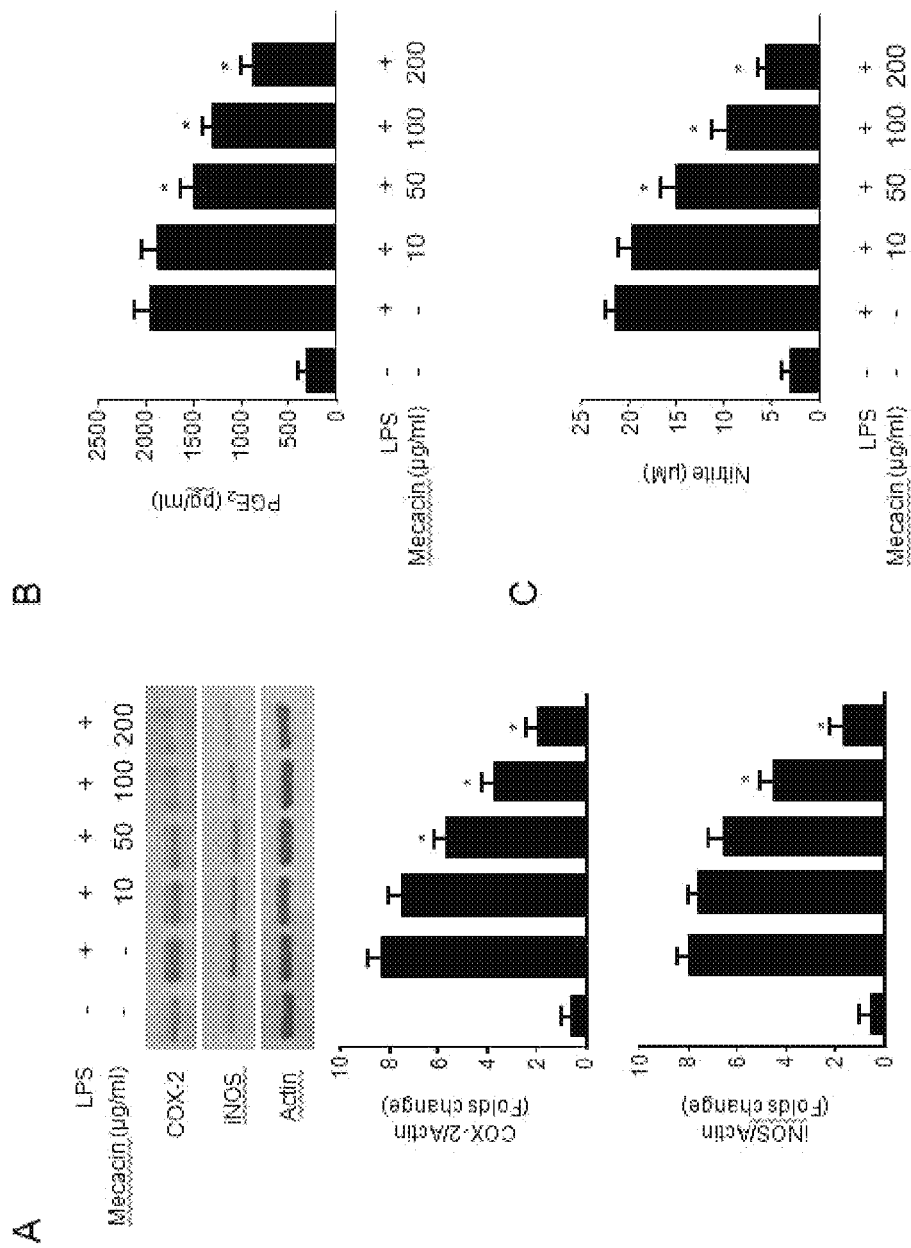
[Fig. 1]

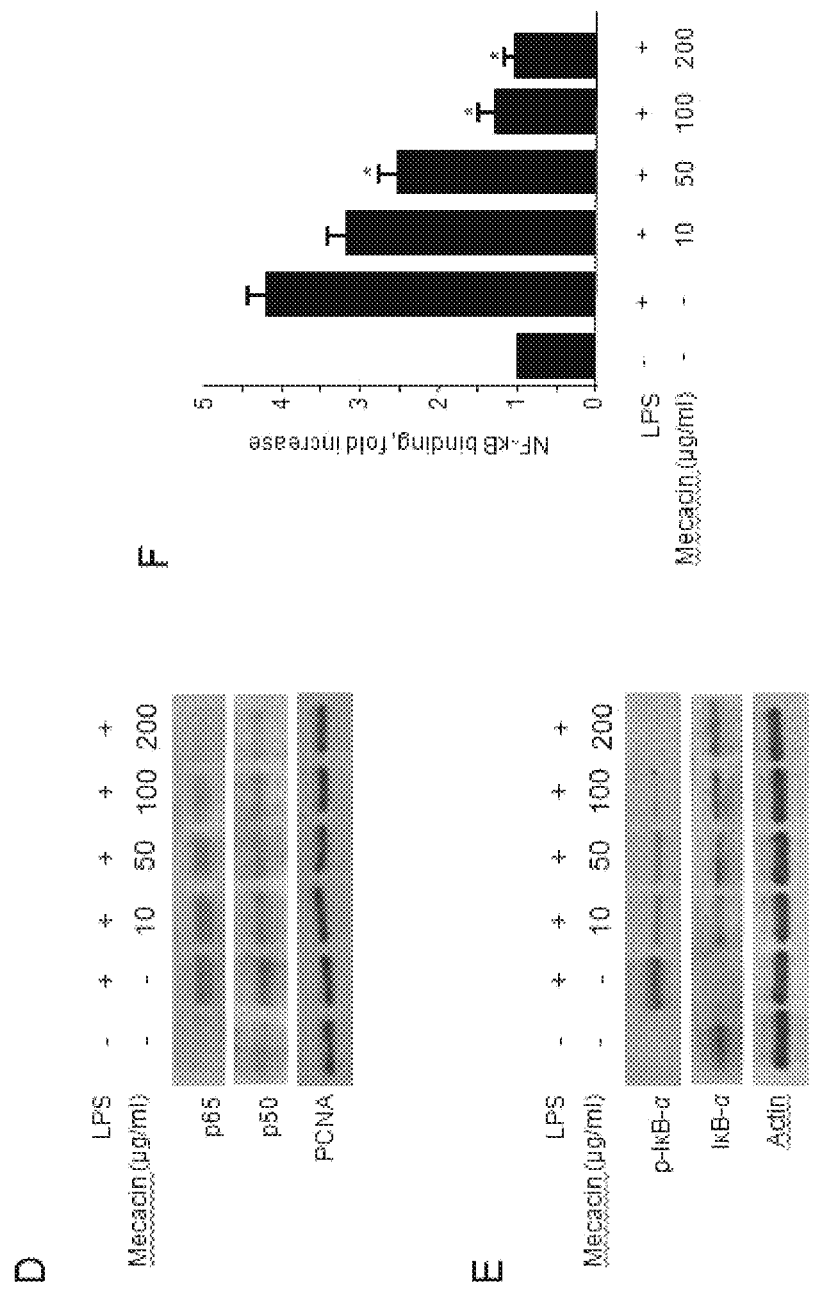
[Fig. 2]

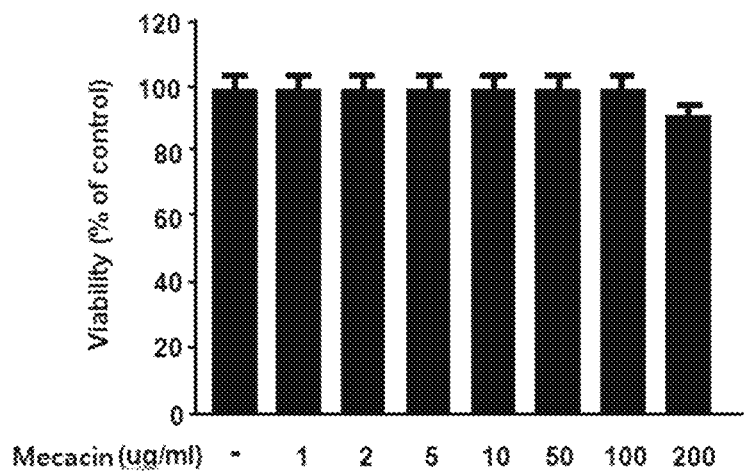
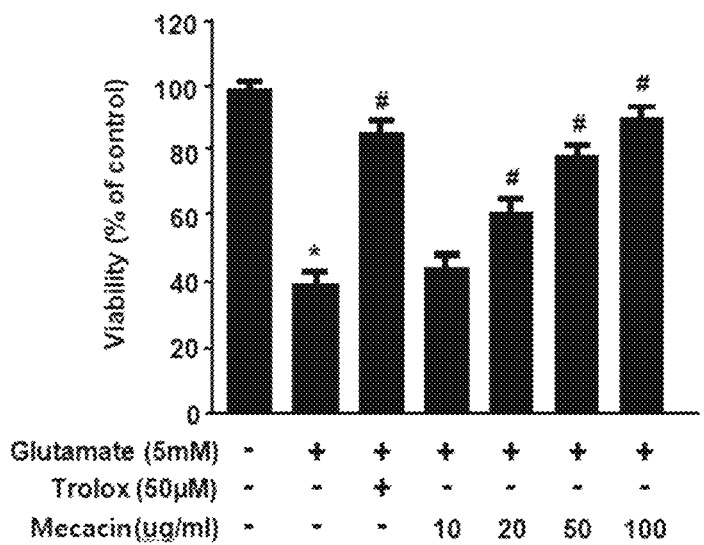
Data are presented as mean ± S.D. values of three independent experiments.
*$P < 0.05$ vs. control.; #$P < 0.05$ vs. Glutamate
[Fig. 3]

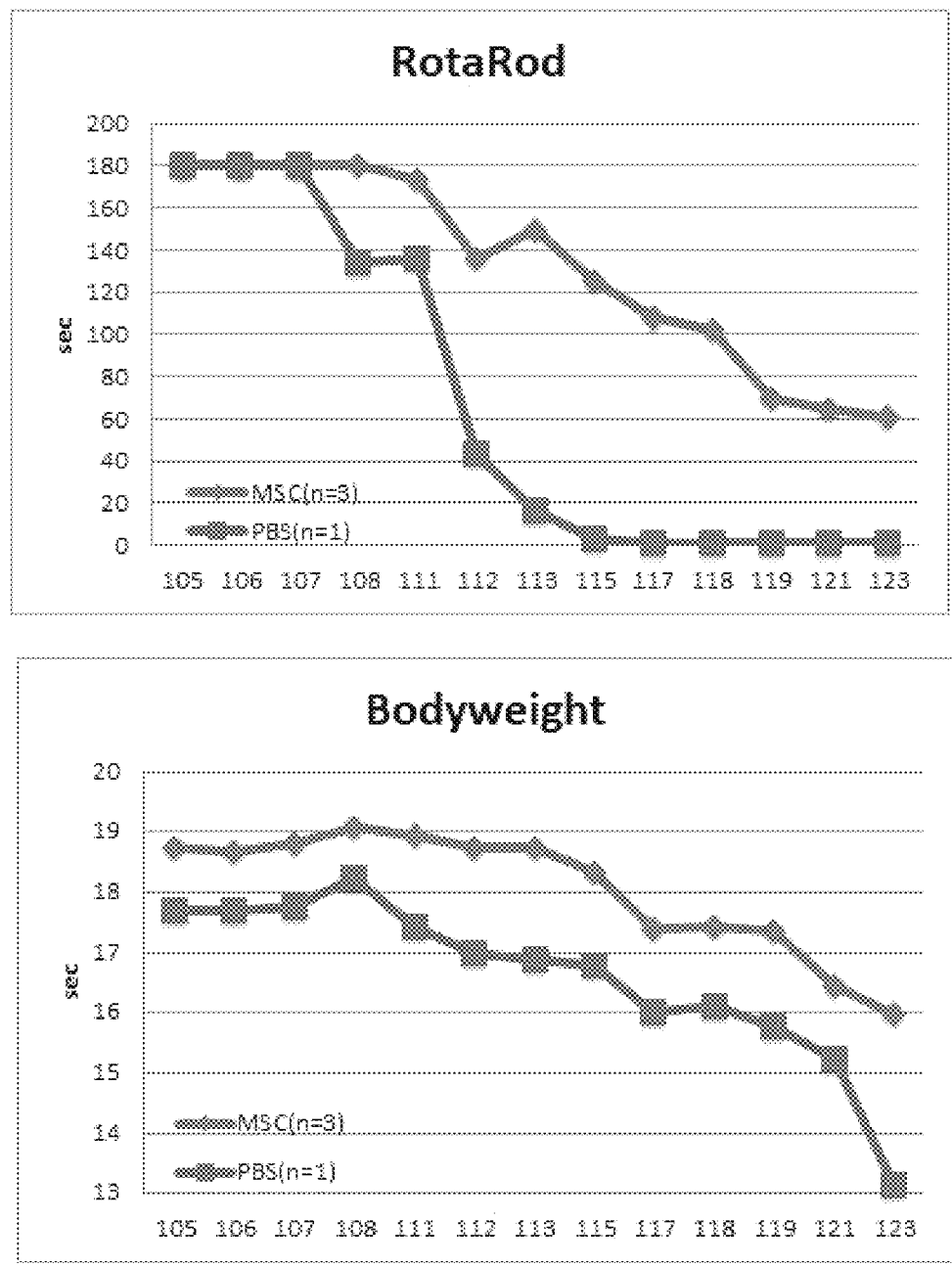
[Fig. 4]

COMPOSITION FOR PREVENTING, ALLEVIATING OR TREATING NEURODEGENERATIVE DISEASES

TECHNICAL FIELD

The present invention relates to a composition for preventing, alleviating or treating neurodegenerative diseases, which contains, as active ingredients, Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum. More specifically, the present invention relates to a composition for preventing, alleviating or treating neurodegenerative diseases, which contains, as active ingredients, 3 to 4 parts by weight of Paeoniae radix, 3 to 4 parts by weight of Glycyrrhizae radix, 1 to 2 parts by weight of Pulvis aconiti tuberis purificatum, and 0.5 to 1 part by weight of each of Curcumae longae rhizoma, Gastrodiae rhizoma, Polygalae radix, Salviae radix, Chaenomeles fructus and Atractylodis rhizoma.

The composition according to the present invention is not cytotoxic, causes no side effects, and has the effect of preventing, alleviating or treating neurodegenerative diseases by alleviating neuroinflammation and protecting neural cells.

BACKGROUND ART

Neurodegenerative diseases include amyotrophic lateral sclerosis (Lou Gehrig's disease), motor neuron disease, dementia, Parkinson's disease, cerebellar atrophy, Creutzfeldt-Jakob disease, and Huntington's disease, and are characterized by neurodegenerative changes in specific areas.

The causes of neurodegenerative disease are still unclear, and it has been reported that the incidence of neurodegenerative diseases increases with age.

Patients with neurodegenerative diseases experience symptoms such as akinesia, sensory disturbance, muscle rigidity, atrophy and convulsions, which make their daily life very difficult and may significantly reduce the quality of life of the patients and their family members. Accordingly, studies have been continuously conducted on therapies against neurodegenerative diseases.

Conventional agents for treating neurodegenerative diseases include Riluzole, Yoo's Neurosolution and the like, and technologies that are being studied at present include bone marrow-derived adult stem cells and the like.

Riluzole is an agent that treats neurodegenerative diseases by inhibiting excessive release of glutamic acid, but causes side effects such as decreased liver function, dizziness, diarrhea, abdominal pain, vomiting, and loss of appetite. Due to such side effects, Riluzole has disadvantages in that the administration thereof is stopped in about 14% of the patients and in that Riluzole is not suitable for long-term administration. In addition, it has been reported that Riluzole is not effective against neurodegenerative diseases.

Yoo's Neurosolution is a therapeutic agent containing the bile acid ursodeoxycholic acid (UDCA), which delivers pure UDCA to brain tissue without modifying its molecular structure, to inhibit brain cell death that causes motor neuron disease, thereby preventing the progression of muscular dystrophy and alleviating symptoms.

However, Yoo's Neurosolution was reported to cause side effects such as vomiting, abdominal pain, diarrhea, dizziness, headache, difficulty in breathing, and nausea, and is therefore also problematic in terms of its effects against neurodegenerative diseases.

Bone marrow-derived adult stem cells are still in clinical trial phases, and are expected to be commercialized after many years of studies.

Therefore, the present applicant seeks to provide a natural material-derived composition which causes no side effects, is not cytotoxic, is suitable for long-term administration, and is highly effective in preventing, alleviating or treating neurodegenerative diseases, thereby completing the present invention.

Natural materials that are used in the present invention include Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum.

Hereinafter, these materials will be described in brief.

Curcumae longae rhizoma is the rhizome of Curcuma longa belonging to the family Zingiberaceae.

Curcumae longae rhizoma contains curcumin, turmerone, arturmerone and the like, and is effective against menstrual irregularity, postpartum abdominal pain, vomiting, piles, hemoptysis, and the like. In addition, it has a blood pressure lowering effect, an antibacterial effect, and the effect of removing extravasated blood.

Gastrodiae rhizoma is the rhizome of Gastrodia elata belonging to the family Orchidaceae.

Gastrodiae rhizoma contains gastrodin, gastrodioside, vanillyl alcohol and the like, and is effective against vomiting, arthralgia and myalgia. In addition, it has a pain-relieving effect, a blood circulation promoting effect, an anti-epileptic effect, etc.

Polygalae radix is the root of Polygala tenuifolia belonging to the family Polygalaceae.

Polygalae radix contains tenuifoliside, onjisaponins A to G, tenuidine, polygalitol and the like, and has expectorant, hypnotic, anti-epileptic, hemolytic, blood pressure-lowering, anticancer, and uterus-stimulating activities.

Salviae radix is the root of Salvia miltiorrhiza belonging to the family Lamiaceae.

Salviae radix contains tanshinones I and II, dihydrotanshinone, cryptotanshinone, methyl tanshinone, methylene, tanshiquinone, and β-sitosterol, and is effective against cardiovascular diseases, hepatitis, diseases, diabetes, and chronic renal disease.

Chaenomeles fructus is the fruit of Chaenomeles sinensis belonging to the family Rosaceae.

Chaenomeles fructus contains liriodendrin, saponin, malic acid, tartaric acid, citric acid, vitamin C, flavonoids, and tannins, and is effective against diarrhea, dysentery, abdominal pain, vomiting, arthritis, sprain, atopic dermatitis, and the like. In addition, it has an appetite improving effect, a nutritional tonic effect, and the like.

Paeoniae radix is the root of Paeonia japonica belonging to the family Ranunculaceae.

Paeoniae radix contains flavonoids, alkaloids, asparagine, methyl salicylate, sterols, tannins, alcohols, etc., and is effective against polyarthritis, hypertension, encephalitis, leukemia, achylia gastric, gout, rheumatism, and the like, and has sedative, pain-relieving, antispasmodic, antipyretic, anti-inflammatory, hemolytic, antiulcer, blood pressure lowering, and coronary vasodilating effects.

Glycyrrhizae radix is the root of Glycyrrhiza uralensis belonging to the family Fabaceae.

Glycyrrhizae radix contains saponin, glycyrrhizin, flavonoids, colloids and the like, and is effective against sore finger, eczema, food poisoning, neurasthenia, heart disease, duodenal ulcer, stomach cramps, gastric ulcer, gastralgia, throat pain, and the like, and has anti-inflammatory, anti-allergic, poison counteracting, antitussive, pain relieving, anti-epileptic, anti-tumor, bodyweight increasing, muscular strength enhancing, blood pressure elevating, hemolytic, antibacterial, and antipyretic effects.

Atractylodis rhizoma is the root of Atractylodes ovate belonging to the family Asteraceae.

Atractylodis rhizome contains beta-eudesmol, atractylone, vitamin A and the like, and is effective against diabetes, pulmonary tuberculosis, rheumatism, gout, arthralgia, myalgia, vomiting and the like. In addition, it has vasodilator, tonic, antibacterial, blood glucose lowering, and anticancer effects.

Aconiti lateralis preparata radix is the root of Aconitum carmichaeli belonging to the family Ranunculaceae.

Aconiti lateralis preparata radix contains hypaconitine, aconitine, mesaconitine and the like, and is effective against chronic dyspepsia, diarrhea, dehydration & electrolyte imbalance, etc. In addition, it has stimulant and heat function enhancing effects.

In prior art documents related to the present invention, Korean Patent Application Publication No. 10-2006-0023885 discloses a composition for treating dementia, which contains, as a main component, Atractylodis rhizoma, Polygalae radix and other kinds of plants, and as a minor component, Paeoniae rubra and other kinds of plants. Korean Patent No. 10-0564904 discloses a composition for treating dementia, which contains, as active ingredients, Glycyrrhizae radix, Atractylodis rhizoma, Paeoniae radix, and other kinds of plants.

In addition, Korean Patent Application Publication No. 10-2004-0023196 discloses a composition containing, as active ingredients, extracts of Paeoniae radix and Glycyrrhizae radix.

The prior art documents as described above relate to compositions either containing Atractylodis rhizome and Polygalae radix or Paeoniae radix and Glycyrrhizae radix, among Curcumae longae rhizome, Gastrodiae rhizoma, Polygalae radix, Salviae radix, Chaenomeles fructus, Paeoniae radix, Glycyrrhizae radix, Atractylodis rhizoma, and Pulvis aconiti tuberis purificatum, which are used in the present invention. However, these prior art documents do not suggest the efficacy of a composition containing Atractylodis rhizome, Polygalae radix, Paeoniae radix and Glycyrrhizae radix together with Curcumae longae rhizome, Salviae radix, Chaenomeles fructus and Pulvis aconiti tuberis purificatum.

DISCLOSURE

Technical Problem

An object of the present invention is to provide a composition containing Curcumae longae rhizome, Gastrodiae rhizoma, Polygalae radix, Salviae radix, Chaenomeles fructus, Paeoniae radix, Glycyrrhizae radix, Atractylodis rhizoma and Pulvis aconiti tuberis purificatum, which reduces pain by relaxing muscles without causing side effects and cytotoxicity, in neurodegenerative diseases, including amyotrophic lateral sclerosis (Lou Gehrig's disease), motor neuron disease, dementia, Parkinson's disease, cerebellar atrophy, Creutzfeldt-Jakob disease, multiple system atrophy, and Huntington's disease; rare intractable neuromuscular diseases, including Charcot-Marie-Tooth disease, Pompe disease and progressive muscular dystrophy; and pain conditions, including musculoskeletal pain, central pain and visceral pain, and which prevents, alleviates or treats the above-described diseases.

Technical Solution

In order to accomplish the above object, the present invention provides a composition for preventing, alleviating or treating neurodegenerative diseases, in which the composition is prepared by a method comprising the steps of: mixing Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum to obtain a mixture, and extracting the mixture to obtain a mixture extract; filtering the mixture extract; concentrating the mixture extract; and drying the mixture extract.

The present invention also provides a composition for preventing, alleviating or treating neurodegenerative diseases, in which the composition is prepared by a method comprising the steps of: extracting Paeoniae radix, Glycyrrhizae radix, and Pulvis aconiti tuberis purificatum to obtain extract 1; extracting Curcumae longae rhizome, Gastrodiae rhizoma, Polygalae radix, Salviae radix, Chaenomeles fructus, and Atractylodis rhizoma to obtain extract 2; mixing extract 1 with extract 2 to obtain an extract mixture; filtering the extract mixture; concentrating the extract mixture; and drying the extract mixture.

In the present invention, the extraction step is performed 1 to 4 times using 30 wt % ethanol at a temperature of 80 to 95° C. for 1 to 5 hours, the 30 wt % ethanol being used in an amount of 500 to 1500 parts by weight based on 100 parts by weight of each of the mixture extract, extract 1 and extract 2, and the concentration step is performed under reduced pressure at a temperature of 5 to 60° C.

The present invention provides a composition for preventing, alleviating or treating neurodegenerative diseases, which is not cytotoxic, causes no side effects, and has the effects of alleviating neuroinflammation and protecting neural cells.

Advantageous Effects

A composition for preventing, alleviating or treating neurodegenerative diseases according to the present invention is not cytotoxic, causes no side effects, and has the effects of alleviating neuroinflammation and protecting neural cells.

The composition containing Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum according to the present invention has a significant effect of reducing pain by relaxing muscles without causing side effects and cytotoxicity, in neurodegenerative diseases, including amyotrophic lateral sclerosis (Lou Gehrig's disease), motor neuron disease, dementia, Parkinson's disease, cerebellar atrophy, Creutzfeldt-Jakob disease, multiple system atrophy, and Huntington's disease; rare intractable neuromuscular diseases, including Charcot-Marie-Tooth disease, Pompe disease and progressive muscular dystrophy; and pain conditions, including musculoskeletal pain, central pain and visceral pain.

DESCRIPTION OF DRAWINGS

FIGS. 1 and 2 are graphs showing the anti-neuroinflammatory effect of a composition (indicated as Mecacin) obtained according to Embodiment 1 of the present invention;

FIG. 3 is a graph showing the results of measuring the cytotoxicity of the composition (indicated as Mecacin) of Embodiment 1 of a present invention and the protective effect of the composition against glutamate neurotoxicity; and FIG. 4 is a graph showing the results of the Rotarod test performed after the animal models with Lou Gehrig's disease were treated with the composition (indicated as MSC) of Embodiment 1 of the present invention.

MODE FOR INVENTION

The terms and words used in the specification and claims should not be interpreted as being limited to typical meanings or dictionary definitions, but should be interpreted as having meanings and concepts relevant to the technical scope of the present invention, based on the principle that an inventor can appropriately define the concept of the terms to describe their invention in the best way.

Accordingly, it should be understood that the experimental examples and reference examples described in the specification are merely examples and do not represent all the technical spirits of the present invention, and thus there may be various equivalents and modifications that can replace the above examples at the time when the present application is filed.

Embodiment 1: Composition (1) for Preventing, Alleviating or Treating Neurodegenerative Diseases (1) Step of Preparing Mixture Extract Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum are mixed, and then extracted to obtain a mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum.

The herbal materials that are used to prepare the mixture extract may be used at varying weight ratios. For example, based on 3 to 4 parts by weight of Paeoniae radix or Glycyrrhizae radix, Pulvis aconiti tuberis purificatum may be used in an amount of 1 to 2 parts by weight, and each of Curcumae longae rhizome, Salviae radix, Chaenomeles fructus, Polygalae radix, Glycyrrhizae radix and Atractylodis rhizome may be used in an amount of 0.5-1 parts by weight, but the present invention is not limited thereto.

To extract a mixture of Curcumae longae rhizome, Gastrodiae rhizoma, Polygalae radix, Salviae radix, Chaenomeles fructus, Paeoniae radix, Glycyrrhizae radix, Atractylodis rhizoma and Pulvis aconiti tuberis purificatum, various methods may be used, including solvent extraction, steam distillation, carbon dioxide supercritical extraction, microwave extraction, percolation extraction, and the like. Preferably, solvent extraction may be used, but is not limited thereto.

Two or more extraction methods may be used to extract the mixture.

Depending on the kind of extraction solvent, the extraction temperature, the extraction time, the amount of solvent used and a method of treating residual components may vary. The extraction solvent may also be selected from various solvents. Extraction solvents that may be used in the present invention include water, ethanol, methanol, fatty oil, glycerin, horse oil, propylene glycol, ether, chloroform, petroleum ether, hexane, benzene, methylene chloride, ethyl acetate, acetone, butanol, isopropanol and the like. Preferably, ethanol may be used, but is not limited thereto.

In addition, two or more solvents having different distribution coefficients may also used together for extraction, and two or more solvents may be used for second-step extraction.

The extraction solvent may be used at varying concentrations. Preferably, the solvent may be used at a concentration of 30 wt %, but is not limited thereto.

The extraction time, the extraction temperature and the number of extractions may also vary over wide range. Preferably, the extraction process may be performed 1 to 4 times at a temperature of 80 to 95° C. for 1 to 5 hours, but is not limited thereto.

(2) Step of Filtering Mixture Extract

The mixture extract of Curcumae longae rhizome, Gastrodiae rhizoma, Polygalae radix, Salviae radix, Chaenomeles fructus, Paeoniae radix, Glycyrrhizae radix, Atractylodis rhizoma and Pulvis aconiti tuberis purificatum is filtered.

For filtration of the mixture extract, various methods may be used, including atmospheric pressure filtration, suction filtration, vacuum filtration, ultrafiltration, microfiltration, and reverse osmosis filtration.

The filtration time, the filtration temperature and the number of filtrations may vary over a wide range.

The filtration process may be performed using methods other than the above-listed methods, and two or more methods may also be used for filtration.

When microfiltration or ultrafiltration is performed, the filter membrane may preferably have a pore size of 50 µm, but is not limited thereto.

(3) Step of Concentrating Mixture Extract

The mixture extract of Curcumae longae rhizome, Gastrodiae rhizoma, Polygalae radix, Salviae radix, Chaenomeles fructus, Paeoniae radix, Glycyrrhizae radix, Atractylodis rhizoma and Pulvis aconiti tuberis purificatum is concentrated.

For concentration of the mixture extract, various methods may be used, including freeze concentration, reduced-pressure concentration, membrane concentration, vacuum concentration, heating concentration, and evaporation concentration. Preferably, reduced-pressure concentration may be used, but is not limited. In addition, two or more concentration methods may also be used.

The concentration process may be performed at varying temperatures. Preferably, the concentration process may be performed at a temperature of 5 to 60° C., but is not limited thereto. Concentration duration and the number of concentrations may also vary over a wide range.

(4) Step of Drying Mixture Extract

The mixture extract of Curcumae longae rhizome, Gastrodiae rhizoma, Polygalae radix, Salviae radix, Chaenomeles fructus, Paeoniae radix, Glycyrrhizae radix, Atractylodis rhizoma and Pulvis aconiti tuberis purificatum is dried.

For drying of the mixture extract, various methods may be used, including shade-drying, sun-drying, hot-air drying, freeze drying, electric drying, and cold-air drying. Two or more drying methods may be used.

The drying temperature, the drying time and the number of drying cycles may vary over a wide range.

Embodiment 2: Composition (2) for Preventing, Alleviating or Treating Neurodegenerative Diseases (1) Step of Preparing Extract 1

Paeoniae radix, Glycyrrhizae radix and Pulvis aconiti tuberis purificatum are mixed, and then extracted to obtain extract 1.

Preparation of extract 1 is performed in the same manner as described in the step of preparing the mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum in Embodiment 1.

The mixing ratio between Paeoniae radix, Glycyrrhizae radix and Pulvis aconiti tuberis purificatum may vary over a wide range. Preferably, based on 3 to 4 parts by weight of Paeoniae radix, Glycyrrhizae radix may be used in an amount of 3 to 4 parts by weight, and Pulvis aconiti tuberis purificatum may be used in an amount of 1 to 2 parts by weight, but the present invention is not limited thereto.

(2) Step of Preparing Extract 2

Curcumae longae rhizome, Gastrodiae rhizoma, Polygalae radix, Salviae radix, Chaenomeles fructus and Atractylodis rhizome are mixed, and then extracted to obtain extract 2.

Preparation of extract 2 is also performed in the same manner as described in the step of preparing the mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum in Embodiment 1.

The mixing ratio between Curcumae longae rhizome, Gastrodiae rhizoma, Polygalae radix, Salviae radix, Chaenomeles fructus and Atractylodis rhizome may vary over a wide range. Preferably, each of Gastrodiae rhizoma, Polygalae radix, Salviae radix, Chaenomeles fructus and Atractylodis rhizome may be used in an amount of 0.5 to 1 part by weight, but is not limited thereto.

(3) Step of Preparing Extract Mixture

Extracts 1 and 2 prepared as described above are mixed to obtain an extract mixture.

(4) Step of Filtering Extract Mixture

The extract mixture is filtered.

Filtration of the extract mixture is performed in the same manner as described in the step of filtering the mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum in Embodiment 1.

(5) Step of Concentrating Extract Mixture

The extract mixture is concentrated.

Concentration of the extract mixture is performed in the same manner as described in the step of concentrating the mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum in Embodiment 1.

(6) Step of Drying the Mixture of Extract 1 and Extract 2

The mixture of extracts 1 and 2 are dried.

Drying the mixture of extracts 1 and 2 is performed in the same manner as described in the step of drying the mixture extract of Curcumae longae rhizome, Gastrodiae rhizoma, Polygalae radix, Salviae radix, Chaenomeles fructus, Paeoniae radix, Glycyrrhizae radix, Atractylodis rhizome and Pulvis aconiti tuberis purificatum in Embodiment 1.

Experimental Example 1: Effect Against Neuroinflammation 1-1. Experimental Method In order to examine the effect of the composition of the present invention against neurodegenerative diseases, the inflammation inhibitory effect of the composition of the present invention against LPS-induced neuroinflammation in microglia BV-2 cells was evaluated.

In this experiment, the composition according to embodiment 1 was used at varying concentrations (10, 50, 100 and 200 μg/ml).

In order to examine the inflammation inhibitory effect of the composition in neural cells, the expression levels of COX-2 and iNOS, which are pro-inflammatory genes, were measured, and the expression levels of PGE2, nitrite, p65, p50, p-IκB-α and NF-κB, which are pro-inflammatory genes, were also analyzed.

1-2. Experimental Results

FIGS. 1 and 2 are graphs showing the anti-neuroinflammatory effect of a composition (indicated as Mecacin) obtained according to Embodiment 1 of the present invention.

As can be seen therein, the experimental results indicated that when the BV-2 cells with LPS-induced neuroinflammation were treated with the composition of the present invention, the secretion of pro-inflammatory proteins such as COX-2 and iNOS was inhibited in a concentration-dependent manner.

In addition, it was shown that the secretion of PGE2, nitrite, p65, p50, p-IκB-α and NF-κB, which are pro-inflammatory genes, was also inhibited in a concentration-dependent manner, when the BV-2 cells with LPS-induced neuroinflammation were treated with the composition of the present invention.

This suggests that the composition according to the present invention has the effect of preventing, alleviating or treating neurodegenerative diseases by inhibiting neuroinflammation.

Experimental Example 2: Effect Against Glutamate Neurotoxicity 2-1. Experimental Method Glutamate is an excitatory neurotransmitter that increases excitation of neural cells and plays an important role in memory and learning.

However, it is known that when glutamate is excessively released, it changes into an excitotoxic compound which kills neural cells, thereby causing neurodegenerative diseases such dementia, Lou Gehrig's disease or the like.

Therefore, in this Experimental Example, the protective effect of the composition of the present invention against glutamate-induced neurotoxicity was evaluated in order to confirm the effect of the composition of the present invention against neurodegenerative diseases.

In the experiment, BV-2 cells were treated with 5 mM of glutamate to induce neurotoxicity and treated with varying concentrations (10, 20, 50 and 100 μg/ml) of the composition of the present invention, and the viability of the cells was measured. As a positive control, Trolox was used.

Meanwhile, in order to whether or not the composition of the present invention is cytotoxic, BV-2 cells were treated with varying concentrations (1, 2, 5, 10, 50, 100 and 200

μg/ml) of the composition of the present invention, and the viability of the cells was measured.

2-2. Experimental Results

FIG. 3 is a graph showing the results of measuring the cytotoxicity of the composition (indicated as Mecacin) of Embodiment 1 of the present invention and the protective effect of the composition against glutamate neurotoxicity.

Specifically, FIG. 3A shows the results of measuring the cytotoxicity of the composition (indicated as Mecacin) of the present invention. As can be seen therein, the cell viability reached 100% even at a concentration of up to 100 μg/ml, indicating that the composition of the present invention is not cytotoxic at a concentration of up to 100 μg/ml. In addition, at a concentration of 200 μg/ml, a cell viability of about 90% was observed.

FIG. 3B shows the results of measuring cell viability after neural cells with glutamate-induced neurotoxicity were treated with the composition of the present invention. As can be seen therein, the cell viability increased with concentration.

Particularly, it could be seen that the group treated with 100 μg/ml of the composition exhibited a better protective effect compared to the positive control Trolox.

Therefore, it can be seen that the composition according to the present invention has the effect of preventing, alleviating or treating neurodegenerative diseases by protecting neural cells from glutamate neurotoxicity.

Experimental Example 3: Effect in Animal Models with Lou Gehrig's Disease 3-1. Experimental Method Lou Gehrig's disease (also known as amyotrophic lateral sclerosis (ALS)) is a neurodegenerative disease that shows symptoms, such as movement disorders, muscle weakness, respiratory failure and the like, due to motor neuron death.

In this Experimental Example, animal models with Lou Gehrig's disease were treated with the composition of Embodiment 1 of the present invention, and then the motor activities of the mice were measured by a Rotarod test.

The Rotarod is a device that evaluates the motor function of a test animal by pacing the test animal on a beam that rotates at a fixed speed or a gradually accelerating speed and measuring the time taken for the test animal to fall. Using the Rotarod, the effect of the composition of the present invention on motor ability improvement was evaluated.

3-2. Experimental Results

FIG. 4 is a graph showing the results of the Rotarod test performed after the animal models with Lou Gehrig's disease were treated with the composition (indicated as MSC) of Embodiment 1 of the present invention.

As can be seen therein, the experimental results indicated that the time taken for the test animal to fall from the rotating beam increased in the test group treated with the composition of the present invention, compared to the untreated control group.

This suggests that the composition according to the present invention improves the motor function of Lou Gehrig's disease animal models.

The invention claimed is:

1. A composition for preventing, alleviating or treating a neurodegenerative disease, the composition containing, as an active ingredient, an extract of a mixture of the herbal materials consisting essentially of Curcumae longae rhizome, Gastrodiae rhizoma, Polygalae radix, Salviae radix, Chaenomeles fructus, Paeoniae radix, Glycyrrhizae radix, Atractylodis rhizome, and Pulvis aconiti tuberis purificatum, wherein the extract of the mixture is contained in the composition at a concentration of 10 to 200 μg/ml and wherein the composition reduces LPS-induced nitrite production in cultured BV2 microglial cells by at least 30% when provided at a concentration of 50 ug/ml, at least 60% when provided at a concentration of 100 ug/ml, and at least 80% when provided at a concentration of 200 ug/ml.

2. A composition as in claim 1 wherein said neurodegenerative disease is selected from Lou Gehrig's Disease, motor neuron disease, dementia, Parkinson's Disease, cerebral atrophy, Creutzfeldt-Jakob Disease, multiple system atrophy, and Huntington's Disease.

3. A composition as in claim 2 wherein said composition alleviates neuroinflammation and protects neural cells.

4. A composition as in claim 2 wherein said neurodegenerative disease is Lou Gehrig's Disease.

5. A composition as in claim 1 wherein said composition contains 3 to 4 parts by weight of Paeoniae radix, 3 to 4 parts by weight of Glycyrrhizae radix, 1 to 2 parts by weight of Pulvis aconiti tuberis purification, and 0.5 to 1 part by weight of each of Curcumae longae rhizome, Gastrodia rhizome, Polygalae radix, Salviae radix, Chaenomeles fructus, and Atractylodis rhizome.

6. A composition as in claim 1 wherein said composition inhibits LPS-induced inflammation and glutamate neurotoxicity in microglial BV-2 cells.

7. A composition as in claim 1 wherein the extract is produced by the steps of:
  (a) extracting the mixture of herbal materials to form an extract;
  (b) concentrating the extract; and
  (c) drying the extract.

8. A composition as in claim 7 wherein the extracting step (a) is performed by solvent extraction, microwave extraction, percolation extraction, steam distillation, or carbon dioxide supercritical extraction.

9. A composition as in claim 8 wherein the extracting step (a) is by solvent extraction in a solvent selected from water, ethanol, methanol, fatty oil, glycerin, horse oil, propylene glycol ether, chloroform, petroleum ether, hexane, benzene, methylene chloride, ethyl acetate, acetone, butanol, and isopropanol.

10. A composition as in claim 9 wherein the solvent is ethanol at 30 wt %.

11. A composition as in claim 10 wherein the extraction process is performed 1 to 4 times at a temperature of 80-95° C. for 1 to 5 hours.

* * * * *